US00PP08284P

United States Patent [19]

Trees

[11] Patent Number: Plant 8,284

[45] Date of Patent: Jun. 29, 1993

[54] GERANIUM PLANT—BSR-177 WHITE CULTIVAR

[75] Inventor: Scott C. Trees, Arroyo Grande, Calif.

[73] Assignee: George J. Ball, Inc., West Chicago, Ill.

[21] Appl. No.: 761,703

[22] Filed: Sep. 18, 1991

[51] Int. Cl.[5] ..... A01H 5/00

[52] U.S. Cl. ..... Plt./87.12

[58] Field of Search ..... Plt./87.12

[56] References Cited

U.S. PATENT DOCUMENTS

P.P. 3,173 5/1972 Knicely et al. ..... Plt. 87.12

P.P. 7,392 12/1990 Schumann ..... Plt. 87.12

*Primary Examiner*—James R. Feyrer

*Assistant Examiner*—E. F. McElwain

*Attorney, Agent, or Firm*—Burns, Doane, Swecker & Mathis

[57] ABSTRACT

A new and distinct tetraploid *Pelargonium*×*hortorum* cultivar named BSR-177 White is provided. This new Zonal Geranium cultivar was the result of a controlled breeding program wherein an unnamed plant designated PAS-W was pollinated by an unnamed plant designated 527-5. The new cultivar forms attractive semi-double pure white florets which contrast well with dark green distinctly zoned foliage. The attractive dark green foliage coloration is well retained even during shipment. The growth habit is inherently compact and self-branching and does not require the use of growth regulators to maintain such growth characteristic.

1 Drawing Sheet

SUMMARY OF THE INVENTION

The present invention comprises a new and distinct Geranium cultivar, botanically known as *Pelargonium*-×*hortorum*, and hereinafter is referred to by the cultivar name BSR-177 White.

The new cultivar is the product of a planned breeding program which had as its objective the creation of a highly productive new Geranium cultivar which exhibits uniform pure white blossoms, dark green foliage, a compact self-branching growth habit, no requirement for the use of a growth regulator, a propensity for rapid rooting, and stable foliage coloration during shipment. Such combination of traits is not believed to have been present in previously available Zonal Geranium cultivars. This objective was satisfactorily fulfilled in the cultivar of the present invention.

The breeding program which resulted in the production of the new cultivar of the present invention was carried out in a controlled environment during 1988 at Santa Maria, Calif., U.S.A. The female parent (i.e., the seed parent) was an unnamed plant designated PAS-W. Such female parent formed semi-double white florets, formed medium green foliage, and was compact and self-branching. The male parent (i.e., the pollen parent) was an unnamed plant designated 527-5. Such male parent formed single blush white florets, formed dark green foliage, and exhibited an upright growth habit. The parentage of the new cultivar can be summarized as follows:

PAS-W×527-5.

The seeds resulting from the above pollination were sown and plantlets were obtained which were physically and biologically different from each other. Selective study which was finalized on Jan. 15, 1989, at Santa Maria, Calif. resulted in the identificaion of a single plant of the new cultivar. This plant initially was designated BSR-177.

It was found that the new cultivar of the present invention:

(a) exhibits attractive pure white semi-double florets,
(b) forms attractive dark green foliage which resists turning to a yellow green coloration during shipment as is common with the Alba and Snowhite (U.S. Plant Pat. No. 5,312) cultivars,
(c) bears distinctly-zoned leaves, and
(d) exhibits an inherently compact and self-branching growth habit in the absence of growth regulators.

Asexual reproduction of the new cultivar by vegetative cuttings initially taken on Feb. 10, 1989, and horticulturally examined in a controlled environment on Apr. 15, 1989, at Santa Maria, Calif., has demonstrated that the characteristics of the new cultivar as herein described are firmly fixed and are retained through successive generations of asexual propagation.

When plant material on the BSR-177 White cultivar is subjected to standard random amplified polymorphic DNA marker analysis (RAPD) using polymerase chain reaction (PCR) and a known unique set of DNA primers, it is found to exhibit a distinctive fingerprint map which is on file at the Ball FloraPlant Division of George J. Ball, Inc. at Arroyo Grande, Calif.

BSR-177 White has not been observed under all possible environmental conditions to date. Accordingly, it is possible that the phenotype may vary somewhat with variations in the environment, such as temperature, light intensity, and day length.

When the new cultivar of the present invention is compared to the Alba cultivar, the Alba cultivar is found to also exhibit semi-double white florets; however, the foliage is medium to light green in coloration rather than dark green. Also, the peduncle coloration at the base of the new cultivar tends to be darker than that of the Alba cultivar (e.g., Green Group 141A and 141B vs. Green Group (143B), and the corolla diameter tends to be slightly larger on the Alba cultivar as specified in greater detail hereafter.

The new cultivar of the present invention is being marketed under the Showcase trademark.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Santa Maria, Calif.

DETAILED DESCRIPTION

The chart used in the identification of colors described herein is the R.H.S. Colour Chart of The Royal Horticultural Society, London, England. Color terminology in common terms precedes the reference to the R.H.S. Colour Chart information. The color values were determined on Jul. 18, 1991 at 10:00 to 11:00 a.m. using a light intensity of 1550 footcandles at Santa Maria, Calif. The plants described were grown under standard greenhouse conditions.

Classification:

*Botanical.*—*Pelargonium* × *hortorum,* cv. BSR-177 White.

*Commercial.*—Zonal Geranium.

INFLORESCENCE

A. Umbel:

*Average diameter.*—Approximately 11 to 12 cm.

*Average depth.*—Approximately 6 to 7 cm.

*Peduncle length.*—Approximately 17.5 to 18.5 cm.

*Pedicel length.*—Approximately 3 to 4 cm.

When five month old plants are grown in the field, the BSR-177 White cultivar commonly possesses approximately 37 to 40 umbels per plant while the Alba cultivar commonly possesses approximately 44 to 47 umbels per plant. Such field grown plants commonly possess approximately 44 to 47 florets per umbel for the BSR-177 White cultivar and approximately 50 to 66 florets per umbel for the Alba cultivar.

B. Corolla:

*Average diameter.*—Approximately 4.5 to 5.0 cm. This can be compared to approximately 5.0 to 5.25 cm. for the Alba cultivar.

*Form.*—Semi-double, commonly 5 petals plus approximately 2 to 5 petaloids. The outer petals commonly are somewhat concave, non-imbricate and measure approximately 2.7 cm. in length and approximately 2.2 cm. in width, and the petaloids commonly are twisted and range in length from approximately 0.5 to 1.75 cm. In contrast the florets of the Alba cultivar commonly possess approximately 5 to 6 large imbricate petals which measure approximately 2.6 cm. in length and approximately 2.1 cm. in width, and 1 or 2 substantially flat petaloids which range from approximately 0.5 to 0.7 cm. in length. Such petals are flatter than those of the BSR-177 White cultivar, and such petaloids are wider and flatter than those of the BSR-177 White cultivar.

*Color (general tonality from a distance of 3 meters)*-.—White, similar to White Group 155D. The color actually appears even whiter than that of White Group 155D, and is not precisely illustrated on the R.H.S. Colour Chart. The florets sometimes blush to a light pink when grown under cool conditions.

*Color (abaxial).*—White, White Group 155D. This is substantially the same as that of the Alba cultivar.

*Color (adaxial).*—White, White Group 155D. This is substantially the same as that of the Alba cultivar.

C. Bud

*Shape.*—Upright, in a hemispheroidal cluster.

*Color (abaxial).*—White, White Group 155A.

*Color (adaxial).*—White, White Group 155D.

D. Reproductive organs:

*Androecium.*—The anthers commonly are approximately 2 to 3 mm. in length. The pollen is orange in coloration, Greyed-Orange Group 169A; and the filaments commonly are of an irregular configuration.

*Gynoecium.*—The pistil length commonly is approximately 8 to 9 mm., there is a single stigma which commonly branches into 5 or 6 parts, and the style length is approximately 3 to 4 mm.

*Fertility.*—It is not fertile. This can be contrasted to the Alba cultivar which occasionally sets fruits under field growing conditions.

E. Spring flowering response period: Approximately 6 to 7 weeks from rooted cuttings under greenhouse conditions maintained at 55° F. at night and 72° F. during the day when potted on March 1st in a soil mix (e.g., Sunshine No. 2 brand soil mix) in 10 cm. pots.

F. Outdoor flower production: Vigorous and freely flowering under outdoor growing conditions with substantially continuous blooming.

G. Durability: More tolerant to rain and wind than the Alba cultivar. The foliage does not tend to yellow under stress conditions as does that of the Alba cultivar. Also, the dark green foliage coloration does not break down during shipment as is common with the foliage coloration of the Alba and Snowhite cultivars.

PLANT

A. Foliage: Darker zoning at the outer margin of the leaves measuring approximately 2 to 3 cm. The foliage and peduncles are of a much darker green than those of the Alba cultivar. Also, the dark green foliage of the BSR-177 White cultivar better withstands a tendency to break down during shipping of cuttings than the yellow-green foliage of the Alba cultivar.

*Form.*—Reniform, cordate base.

*Margin.*—Crenate.

*Color (abaxial).*—Dark green, Green Group 139A at the outer margins or zones (e.g., outer 2 to 3 cm.) and Yellow-Green Group 147A at the center of the leaves. This compares to a margin coloration of Green Group 137A for the Alba cultivar.

*Color (adaxial).*—Medium green, Yellow-Green Group 146A, having veins of Yellow-Green Group 146B. This compares to a coloration of Green Group 137C for the Alba cultivar.

B. General appearance and form:

*Internode length.*—Commonly varies from approximately 2 to 3 cm.

*Branching pattern.*—Compact and basal branching. No pinching or the use of growth regulator is required to obtain compact and self-branching plants.

*Height.*—Approximately 20 to 25 cm. above a 10 cm. pot when the blossoms first open.

I claim:

1. A new and distinct cultivar of Geranium plant named BSP-177 White, substantially as herein shown and described, which:

(a) exhibits attractive pure white semi-double florets,
(b) forms attractive dark green foliage which resists turning to a yellow green coloration during shipment as is common with the Alba and Snowhite (U.S. Plant Pat. No. 5,312) cultivars,
(c) bears distinctly-zoned leaves, and
(d) exhibits an inherently compact and self-branching growth habit in the absence of growth regulators.

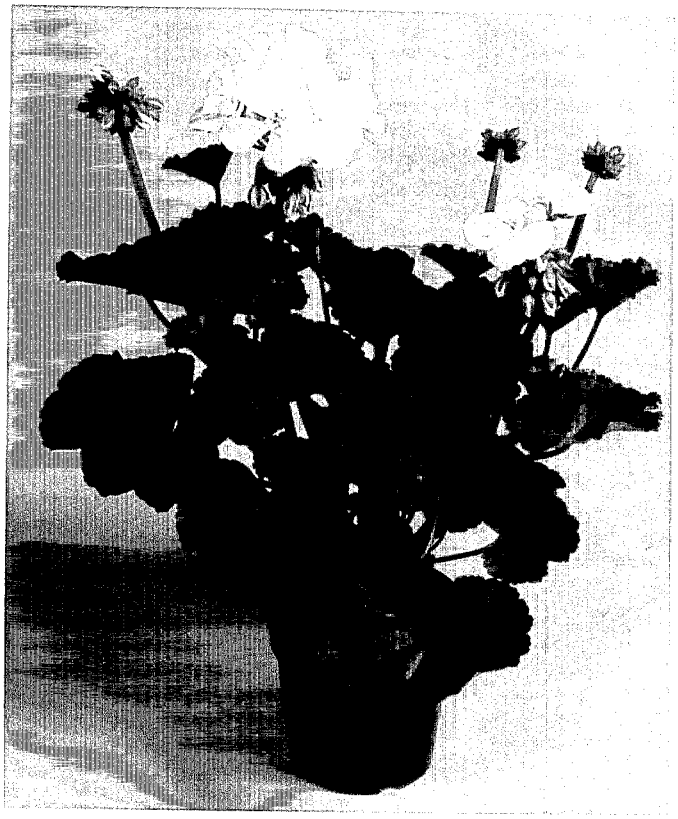

* * * * *